US009456757B1

(12) United States Patent
Zheng et al.

(10) Patent No.: US 9,456,757 B1
(45) Date of Patent: Oct. 4, 2016

(54) NONINVASIVE MONITORING HYDROCEPHALUS, CEREBRAL EDEMA, AND INTRACRANIAL BLEEDING USING ELECTROMAGNETIC WAVE PROPAGATION PROPERTIES

(71) Applicant: Yi Zheng, Cold Spring, MN (US)

(72) Inventors: Yi Zheng, Cold Spring, MN (US);
Eugene Zheng, Cold Spring, MN (US);
Weining Hu, Cold Spring, MN (US)

( * ) Notice: Subject to any disclaimer, the term of this patent is extended or adjusted under 35 U.S.C. 154(b) by 497 days.

(21) Appl. No.: 13/573,724

(22) Filed: Oct. 4, 2012

Related U.S. Application Data

(60) Provisional application No. 61/542,314, filed on Oct. 3, 2011.

(51) Int. Cl.
| | |
|---|---|
| *A61B 5/03* | (2006.01) |
| *A61B 5/02* | (2006.01) |
| *A61B 5/05* | (2006.01) |
| *A61B 5/00* | (2006.01) |

(52) U.S. Cl.
CPC .......... *A61B 5/031* (2013.01); *A61B 5/02042* (2013.01); *A61B 5/05* (2013.01); *A61B 5/7225* (2013.01); *A61B 5/7228* (2013.01); *A61B 5/7282* (2013.01)

(58) Field of Classification Search
CPC ........ A61B 5/035; A61B 5/05; A61B 5/053; A61B 5/0507; A61B 5/0536; A61B 5/0537; A61B 5/4064; A61B 8/0808
USPC .......................................... 600/547
See application file for complete search history.

(56) References Cited

U.S. PATENT DOCUMENTS

| | | | | |
|---|---|---|---|---|
| 4,270,545 A * | 6/1981 | Rodler | | 600/407 |
| 4,690,149 A * | 9/1987 | Ko | | 600/409 |
| 4,819,648 A * | 4/1989 | Ko | | 600/409 |
| 5,807,270 A * | 9/1998 | Williams | | 600/547 |
| 7,638,341 B2 * | 12/2009 | Rubinsky | | A61B 5/05 324/694 |
| 8,062,224 B2 * | 11/2011 | Ragauskas et al. | | 600/448 |
| 2010/0049077 A1 * | 2/2010 | Sadleir | | A61B 5/0002 600/547 |
| 2012/0203134 A1 * | 8/2012 | Kinrot | | A61B 5/0265 600/547 |
| 2013/0190599 A1 * | 7/2013 | Wyeth et al. | | 600/409 |

* cited by examiner

*Primary Examiner* — Adam J Eiseman
(74) *Attorney, Agent, or Firm* — Merchant & Gould P.C.

(57) ABSTRACT

The present invention describes a system and methods to monitor hydrocephalus and cerebral edema in noninvasive or minimum invasive ways. The system monitors the changes of electromagnetic wave propagations in brain tissues changed by the tissue pathological statues. One of the tissue properties monitored is the tissue permittivity that determines the wave propagation velocity. By avoiding the tissue conductivity that has variations due to many different reasons including non-pathological factors, this approach has advantages of acquiring reliable pathological information of brain tissue and being independent to electrode properties and skin conditions. Several parameters are defined to quantitatively measure and assess hydrocephalus and cerebral edema: relative phase shift (RPS), travel-time difference (TTD), and change of relative wave velocity. The parameters are defined and normalized in distance and time for measuring relative changes for the monitoring applications. The method includes non-invasive and minimum invasive approaches. Amplitude modulated wave and coded waves are used to reduce interference and effectively detect small changes of tissue properties in preferred frequency ranges.

20 Claims, 6 Drawing Sheets

Block diagram of monitoring system for hydrocephalus and cerebral edema

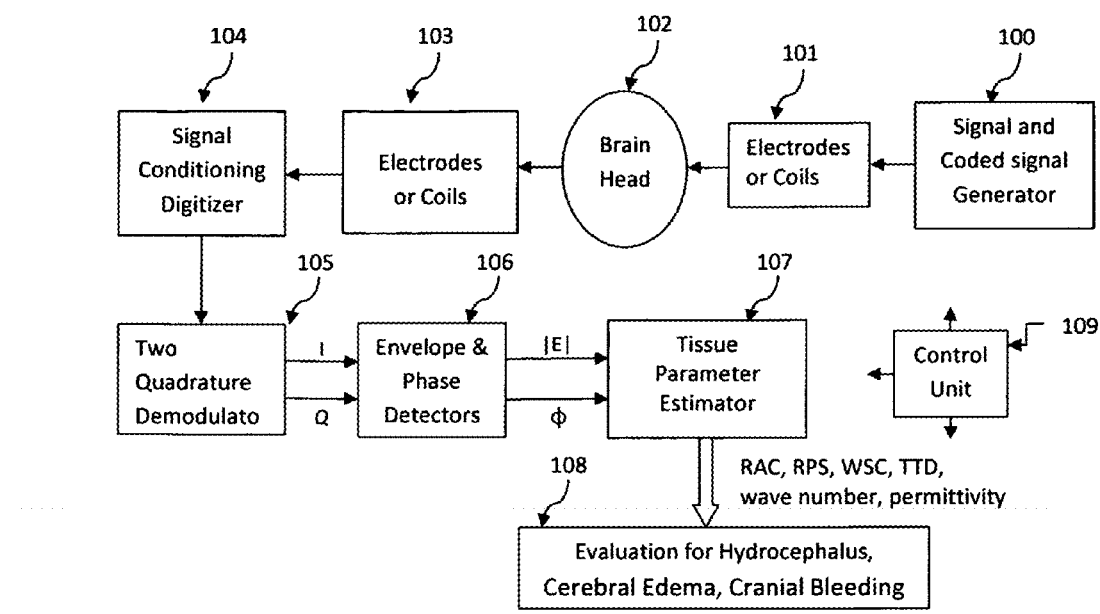
Fig. 1. Block diagram of monitoring system for hydrocephalus and cerebral edema

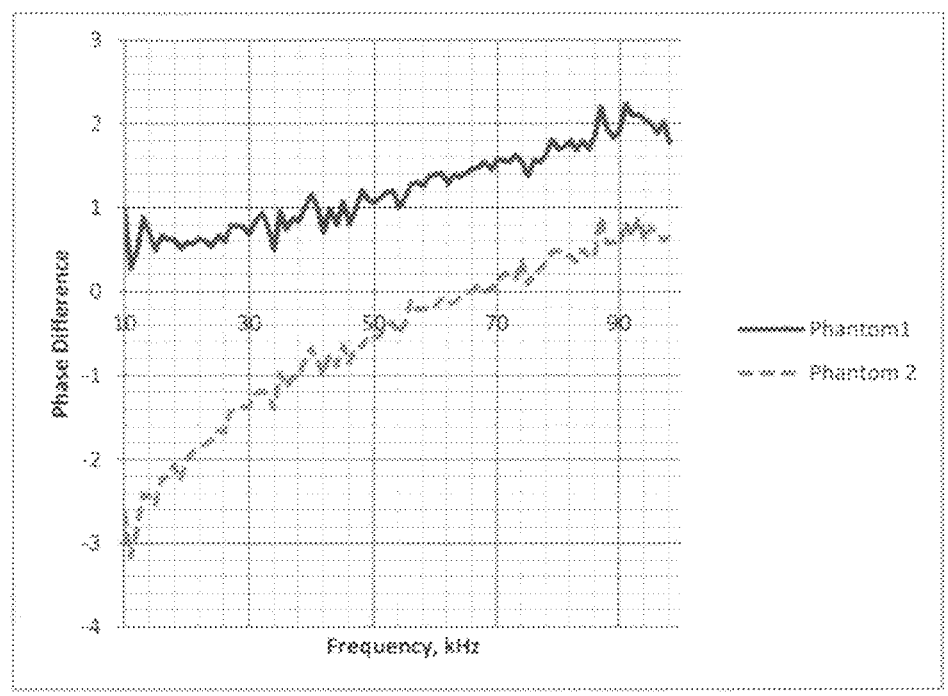
Fig. 2. Phase changes for different ammounts of blood in phantoms made by pig skin powder.

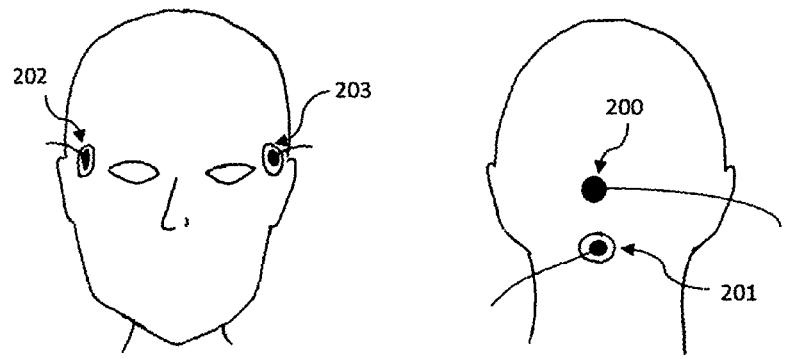
Fig.3 Illustrative example of non-invasive application of the electrodes for emitting and receiving electromagnetic waves.

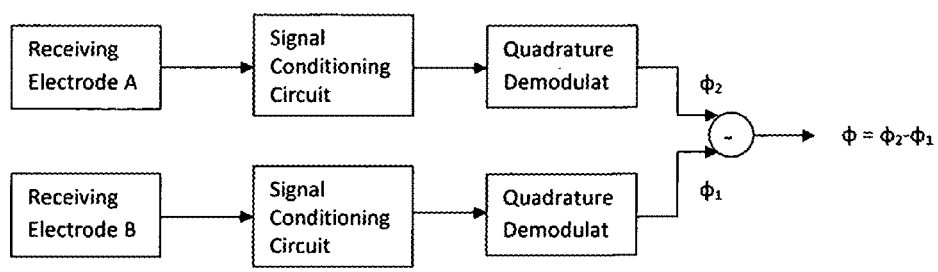
Fig. 4. Two receiving electrodes to detect the phase difference between two locations for 4-electrode configuration

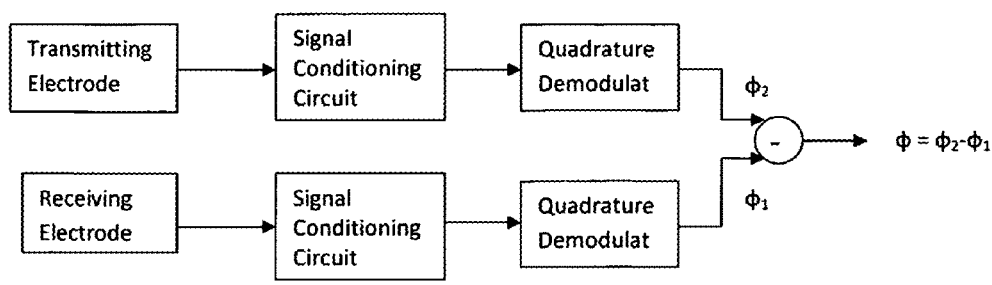
Fig. 5. One receiving electrodes to detect the phase difference between two locations for 3-electrode configuration

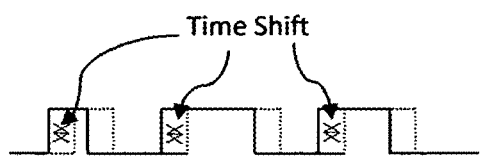
Fig. 6. Using coded wave to detect the time shift due to the brain tissue

NONINVASIVE MONITORING HYDROCEPHALUS, CEREBRAL EDEMA, AND INTRACRANIAL BLEEDING USING ELECTROMAGNETIC WAVE PROPAGATION PROPERTIES

CROSS-REFERENCE TO RELATED APPLICATIONS

This application claims the benefit of Provisional Patent Application No. 61/542,314, filed Oct. 3, 2011 by Yi Zheng, Eugene E. Zheng, and Weining Hu.

BACKGROUND OF THE INVENTION

This invention is generally related to measuring the properties of electromagnetic'wave propagating through brain tissue, and assessing pathological statues of brain, and more specifically related to monitoring hydrocephalus, cerebral edema, and intracranial bleeding. The properties include and not limited to propagation time, travel velocity, complex wave number, phase shift, complex impedance and several parameters defined in this invention. Methods to minimize impacts of electrodes are proposed.

The condition known as hydrocephalus is described as the excessive build-up of the cerebrospinal fluid (CSF) in the brain cavities or ventricles. Under normal conditions, CSF is crucial to the functioning of the brain. It transports nutrients and wastes to and from the brain and creates a protective cushion of liquid. But an over-accumulation of CSF puts disproportionate pressure on the brain and can lead to brain cell and tissue damage. Thus, medical conditions that directly interrupt the regular flow and absorption of CSF into the bloodstream create the overabundance of CSF that ultimately leads to hydrocephalus.

Hydrocephalus has the potential of affecting people of all ages and can be categorized into two main groups: congenital hydrocephalus and acquired hydrocephalus. Congenital hydrocephalus is present at birth and can be the result of genetic abnormalities, prematurity, or influences during the fetal growth period. In contrast, acquired hydrocephalus develops over the course of a person's lifetime from the causes commonly, but not limited to, vascular disease, head injury or head trauma. Two sub-categories of hydrocephalus that primarily affect adults through strokes, hemorrhages, or head trauma are called hydrocephalus ex-vacuo and normal pressure hydrocephalus (NPH).

Although there isn't a national registry for citizens with hydrocephalus, there are some estimates to the significance of this condition within the nation's population. The National Institute of Neurological Disorders and Stroke branch of National Institute of Health estimates that about 1 in every 500 children are born with the condition. And recent statistics show that NPH is the origin of dementia in five percent of people over the age of 70 suffering from dementia.

When diagnosing hydrocephalus, most physicians utilize CT or MRI scans of the head. On the other hand, monitoring techniques currently consist mainly of invasive methods such as intracranial pressure monitoring, lumbar punctures (LP), or measuring CSF impedance using electrodes inserted in the CSF. In these procedures, a hole is required to assess the intracranial environment and sometimes LP can cause brain herniation & death. Recently, transcranial sonography (TCS) has been developed to noninvasively evaluate hydrocephalus, based on medical ultrasound technology. All of the above methods do not provide 24 hour bedside monitoring.

Another similar condition to hydrocephalus is cerebral edema. In response to brain injury such as trauma and infection, cerebral edema can result from the brain tissue swelling with excess water similar to how our ankles or knees swell after an injury. However, unlike our ankles or knees, our brain is surrounded by a thick and rigid skull that doesn't leave room for expansion and thus leads to an increase in intracranial pressure. If left unrecognized and untreated, cerebral edema can lead to permanent damage or death.

Another condition is intracranial bleeding due to head injury or trauma or surgery. The bleeding condition should be closely monitored to provide critical information for patient care.

It is desirable to have a method and a system of continuously monitoring hydrocephalus, cerebral edema, and cranial bleeding at a patient's bedside 24 hours a day in intensive care units. The system needs to be low cost and easy to use, and allows the automated monitoring and minimum intervention.

SUMMARY OF THE INVENTION

The present invention describes a system and a method to monitor hydrocephalus, cerebral edema, and intracranial bleeding in a noninvasive way.

One aspect of the present invention is a system of noninvasively monitoring hydrocephalus, cerebral edema, and intracranial bleeding comprising of a source emitting electromagnetic waves to brain tissue, a detector detecting said wave that propagates through said tissue, a signal conditioning unit amplifying and filtering said wave, a quadrature detector estimating magnitude and phases of said wave, and a parameter estimator calculating the complex wave number, relative attenuation coefficient (RAC), relative phase shift (RPS), wave speed change (WSC), and travel-time difference (TTD) of said brain, and assessing status of hydrocephalus and cerebral edema.

In accordance with yet another aspect of the present invention, a method of noninvasively monitoring hydrocephalus, cerebral edema, and intracranial bleeding comprises of selecting electromagnetic wave, selecting a configuration of electrodes or coils applied to head surface, applying electrodes or coils emitting said wave to brain tissue, selecting and applying electrodes or coils for receiving said wave that propagates through brain tissue, and calculating the complex wave number, RAC, RPS, WSC and TTD of said brain tissue, and assessing status of hydrocephalus, cerebral edema, and intracranial bleeding.

According to a more specific aspect of the present invention, a method of increasing the sensitivity and specificity of monitoring status of hydrocephalus, cerebral edema, and intracranial bleeding comprises of detecting the complex wave number of electromagnetic waves that propagate through brain tissue and are altered by the changed volume of cerebrospinal fluid or cerebral edema condition or intracranial bleeding.

According to a more specific aspect of the present invention, a method of increasing the sensitivity and specificity of monitoring status of hydrocephalus, cerebral edema, and intracranial bleeding comprises of detecting the relative phase shifts (RPS) of electromagnetic waves that propagate through brain tissue and are altered by the changed volume of cerebrospinal fluid or cerebral edema condition, or intracranial bleeding.

According to a more specific aspect of the present invention, a method of increasing the sensitivity and specificity of monitoring status of hydrocephalus, cerebral edema, and intracranial bleeding comprises of detecting the relative attenuation coefficient (RAC) of electromagnetic waves that propagate through brain tissue and is altered by the changed volume of cerebrospinal fluid or cerebral edema condition, or intracranial bleeding.

According to yet a more specific aspect of the present invention, a method of increasing the sensitivity and specificity of monitoring status of hydrocephalus, cerebral edema, and intracranial bleeding comprises calculating the travel time delay (TTD) of electromagnetic pulses that propagated through brain and assessing status of hydrocephalus, or cerebral edema, or intracranial bleeding.

According to yet a more specific aspect of the present invention, a method of increasing the sensitivity and specificity of monitoring status of hydrocephalus, cerebral edema, and intracranial bleeding comprises of calculating the wave speed change (WSC) of brain tissue and assessing status of hydrocephalus, or cerebral edema, or intracranial bleeding.

According to yet a more specific aspect of the present invention, a method of increasing the sensitivity and specificity of monitoring status of hydrocephalus, cerebral edema, and intracranial bleeding comprises of generating coded electromagnetic signals and measuring the changes of the coded wave propagating through brain for assessing the status of hydrocephalus, or cerebral edema, or intracranial bleeding.

According to yet a more specific aspect of the present invention, a method of increasing the sensitivity and specificity of monitoring status of hydrocephalus, cerebral edema, and intracranial bleeding comprises of applying a head band attached with transmitter electrodes or coils for transmitting electromagnetic signals and measuring the changes of RPS, RAC, WSC, TTD, and wave number of brain tissue for assessing the status of hydrocephalus, or cerebral edema, or intracranial bleeding.

According to yet a more specific aspect of the present invention, a method of increasing the sensitivity and specificity of monitoring status of hydrocephalus, cerebral edema, and intracranial bleeding comprises of applying a pair of ear plug coils that are used as transmitter and receiver electrodes for transmitting electromagnetic signals and measuring changes of RPS, RAC, WSC, TTD, and wave number of brain tissue for assessing the status of hydrocephalus, or cerebral edema, or intracranial bleeding.

According to yet a more specific aspect of the present invention, a method of increasing the sensitivity and specificity of monitoring status of hydrocephalus, cerebral edema, and intracranial bleeding comprises of applying multiple electrodes for transmitting electromagnetic signals, removing electrode dependence, and measuring changes of RPS, RAC, WSC, TTD, and wave number of brain tissue at different locations for assessing the status of hydrocephalus, or cerebral edema, or intracranial bleeding of brain tissue at different locations.

BRIEF DESCRIPTION OF THE DRAWINGS

FIG. 1 is a graphic representation of block diagram of the monitoring system for hydrocephalus, cerebral edema, and intracranial bleeding.

FIG. 2 is an illustrative graphic representation of phase shifts for tissue phantoms having different amounts of blood, measured by said system described by this invention in a frequency range from 10 kHz to 100 kHz.

FIG. 3 is an illustrative example of non-invasive application of the electrodes for emitting and receiving electromagnetic waves.

FIG. 4 shows that two receiving electrodes are used to detect the phase difference between two locations for 4-electrode configuration.

FIG. 5 shows that one receiving electrode is used to detect the phase difference between two locations for 3-electrode configuration.

FIG. 6. is an illustrative example to use coded wave for detecting the time shift due to the brain tissue.

DETAILED DESCRIPTION OF THE INVENTION

Pathological status of biological tissues has an impact on the propagation of electromagnetic waves. The impact includes changes of wave velocity, wave length, wave number, wave magnitude and phase, etc.

The propagation of electromagnetic waves is governed by Maxwell equations:

$$\nabla \times E = -\frac{\partial B}{\partial t} \qquad (1)$$

$$\nabla \times H = J + \frac{\partial D}{\partial t} \qquad (2)$$

$$\nabla \cdot B = 0 \qquad (3)$$

$$\nabla \cdot D = \rho_v \qquad (4)$$

where
E=electric field strength (volts per meter)
D=electric flux density (coulombs per square meter)
H=Magnetic field strength (amperes per meter)
B=Magnetic flux density (Webers per square meter or Teslas)
J=electric current density (amperes per square meter)
$\rho_v$=electric charge density (coulombs per cubic meter)

For a given field strength, flux density is different for different mediums. This is described by the constitution relations:

$$D = \in E \qquad (5)$$

$$B = \mu H \qquad (6)$$

where $\in$ is permittivity and $\mu$ is permeability of the medium. For air, $\in = \in_0 = 8.85 \times 10^{-12}$ F/m, $\mu = \mu_0 = 4\pi \times 10^{-7}$ H/m.

For most mediums including biological tissues, $\mu = \mu_0$ and $\in$ is a complex number that is a function of conductivity a and dielectric constant $\in_r$. Thus, the complex permittivity $\in$ is:

$$\varepsilon = \varepsilon_r \varepsilon_0 - j\frac{\sigma}{\omega} = \varepsilon' - j\varepsilon'' \qquad (7)$$

The CSF has very different dielectric constant and conductivity than that of brain white matter and brain grey matter. The conductivity of CST is higher than that of brain white matter and brain grey matter. The dielectric constant of CST is less than those of brain white matter and brain grey matter. On the other hand, the blooding tissue has a higher dielectric constant than those of the brain white and grey matters. In general, the wave propagation speed is inversely proportional to the dielectric constant, and the wave attenuation is proportional to the conductivity. These are fundamental concepts to monitoring changes of CSF in brain and bleeding condition. Because the parameters of electromagnetic wave propagation through brain are related to the dielectric constant and conductivity, which can be used to evaluate the changed volume of cerebrospinal fluid or cerebral edema condition or intracranial bleeding condition.

As shown later, the dielectric constant determines the wave propagation speed and the conductivity causes the wave loss along the prorogation pathway. For most dissipative mediums, the loss is not only caused by conductivity, there is a "dielectric loss" due to the "friction" among polarized molecules, which is determined by the chemical and biological content of the medium. Loss tangent is introduced to characterize the inherent dissipation of electromagnetic energy:

$$\tan\delta = \frac{\varepsilon''}{\varepsilon'} \tag{8}$$

For time-harmonic fields when a single frequency is concerned, the time derivative is replaced by $j\omega$ where angular $\omega=2\pi f$ and f is the frequency in Hz. Thus the real time-space function of E(r,t) and H(r,t) can be represented by complex vectors E(r) and H(r), which contain all information about E(r,t) and H(r,t) at a given frequency:

$$E(r,t)=Re\{E(r)e^{j\omega t}\} \tag{9}$$

$$H(r,t)=Re\{H(r)e^{j\omega t}\} \tag{10}$$

Induction of the complex vectors removes the dependence of time and allows a simple approach to find the solution of the Maxwell equations. If the tissue medium is devoid of any source which is the case in brain tissue, Maxwell equations become:

$$\nabla \times E = -j\omega\mu H \tag{11}$$

$$\nabla \times H = j\omega\in E \tag{12}$$

$$\nabla \cdot H = 0 \tag{13}$$

$$\nabla \cdot E = 0 \tag{14}$$

From (11) and (12) we have $\nabla \times \nabla \times E = \omega^2 \in \mu E$. Recognizing $\nabla \times (\nabla \times E) = \nabla(\nabla \cdot E) - \nabla^2 E$ and $\nabla \cdot E = 0$, we have:

$$\nabla^2 E + k^2 E = 0 \tag{15}$$

where k is a complex wave number, $$k = \omega\sqrt{\mu\in} = k_r - jk_l \tag{16}$$

The solution of (15) for plane wave is:

$$E = \hat{r}E_0 e^{-jk\cdot r} = \hat{r}E_0 e^{-k_l\cdot r}e^{-jk_r\cdot r} \tag{17}$$

where r is a distance vector. (17) shows that the amplitude of wave attenuates (loss) as distance increases because of $k_l$, and the phase shift increases as distance increases because of $k_r$.

For spherical wave, the field strength is further attenuated in the rate of $1/(4\pi r^2)$, because the surface area increases as the distance increases.

The real time-space function of E fields is:

$$E(r,t)=Re\{E(r)e^{j\omega t}\}=\hat{r}E_0 e^{-k_l\cdot r}\cos(\omega t - k_r\cdot r) \tag{18}$$

To quantify the electromagnetic wave propagating through the brain tissue having different conductivities and dielectric constants due to different pathological conditions, we define Relative Attenuation Coefficient (RAC) based on the magnitude information:

$$RAC = \frac{1}{r\omega}\log_e\left(\frac{|E_1|}{|E_2|}\right) = \frac{1}{\omega}(k_{l,2} - k_{l,1}) \tag{19}$$

where $k_{l,1}$ is the imaginary part of the complex wave number $k_1$, which is a baseline of conductivities and dielectric constants measured early. $k_{l,2}$ is the imaginary part of the complex wave number $k_2$, which is recently measured. Because every brain is structured differently, the baseline and measurement for the relative change are important for the monitoring processing based on the priori knowledge of a known condition, recognizing that the diagnosis is done by using MRI or CT or other methods.

The RAC is obtained by taking a ratio between the received field intensity measured early or recently, scaled by the distance and frequency. It is recognized that the field intensity is the derivative of the potential field of the electromagnetic wave. Thus, the ration of the field intensity can be related to the received amplitude. The amplitude $|E|$ and phase $\phi$ of received signals can be obtained by a quadrature demodulator as shown in FIG. 1:

$$I=LPF\{E(r,t)\cos(\omega t)\}=\hat{r}\frac{1}{2}E_0 e^{-k_l\cdot r}\cos(k_r\cdot r) \tag{20}$$

$$Q=LPF\{E(r,t)\sin(\omega t)\}=\hat{r}\frac{1}{2}E_0 e^{-k_l\cdot r}\sin(k_r\cdot r) \tag{21}$$

$$|E|=\frac{1}{2}E_0 e^{-k_l\cdot r}=\sqrt{I^2+Q^2} \tag{22}$$

$$\phi = k_r \cdot r = \tan^{-1}\left(\frac{Q}{I}\right) \tag{23}$$

where LPF represents the operation of a low pass filter to remove the carrier frequency of $\omega$. Thus, $$RAC = \frac{1}{|r|\omega}\log_e\left(\sqrt{\frac{I_1^2+Q_1^2}{I_2^2+Q_2^2}}\right) \tag{24}$$

where $|r|$ is a distance between the transmitter electrode and receiver electrode. It is recognized that the field intensity measured by using electrodes is also impacted by the impedance between the electrodes and skins, an undesirable feature. This problem is addressed later.

While the magnitude of electromagnetic waves may be impacted by some uncontrollable factors such as variable impendence of skin and contacting conditions between electrodes and skin, travel speeds and phases of electromagnetic waves often provide robust information of the wave propagation. Because the synchronized demodulation is used, transmitted wave and demodulating wave have the same initial phase. Thus, $k_r$ can be obtained:

$$k_r = \frac{\phi}{|r|} \tag{25}$$

$k_r$ is related to the phase change of the wave, which provides robust information of medium with reduced issues of contacting surface between skin and electrodes. Thus, we define Relative Phase Shift (RPS):

$$RPS = \frac{1}{|r|\omega}(\phi_2 - \phi_1) = \frac{1}{\omega}(k_{r,2} - k_{r,1}) \qquad (26)$$

where $k_{r,1}$ is real part of the complex wave number $k_1$, which is a baseline measured early and $k_{r,2}$ is real part of the complex wave number $k_2$, which is measured later. The frequency dependence of the wave number is removed by $1/\omega$. For the weak conductive brain tissue, $$k_r \approx \omega\sqrt{\mu\varepsilon} \qquad (27)$$

$$k_I \approx \frac{\sigma}{2}\sqrt{\frac{\mu}{\varepsilon}} \qquad (28)$$

Thus, the change of the RPS represents the change of the dielectric constant of the pathological condition of brain tissue.

In general, the dielectric constant of blood is higher than that of brain tissue and that of the CSF is lower than that of brain tissue. The dielectric constants of all tissues are high in low frequency. The dielectric constant can be in the order of several thousands in the frequency range of kHz, while the dielectric brain tissue may be in the order of hundreds and thousands in the same frequency range. Thus, the changes of the brain pathological conditions can be monitored by examining the changes of PRS.

Experiments were conducted to verify this concept. As shown in FIG. 2, the phase changes from its original values are different for different amounts of blood in four different phantoms using pig skin powder. The phase shifts represent different dielectric constants, different wave speeds, different wave numbers, and different wave travel time, etc. A higher amount of blood causes a larger phase shifts. The similar properties were also observed in several and tens of MHz frequency range. This phase shifts were also observed for tissue phantoms with different water contents and different dielectric constants. The experiment data were acquired with a system that is described by FIG. 1. Electrodes were attached to the phantoms for the transmitting and receiving the electromagnetic wave during the experiment.

The changes of CSF and brain tissue can be also measured by the changes of the speed of the electrical magnetic wave propagating through brain tissue. The wave speed is found by examining the wave with a constant phase of (18), $$\frac{d(\omega t - k_r r)}{dt} = \omega - k_r \frac{dr}{dt} = 0 \qquad (29)$$

$$v = \frac{dr}{dt} = \frac{\omega}{k_r} = \frac{1}{\sqrt{\mu\varepsilon}} \qquad (30)$$

Thus, the speed change of electromagnetic wave propagating through the brain tissue indicates the changes of dielectric constant of brain tissue. We define a Wave Speed Difference:

$$WSD = v_1 - v_2 = \omega\frac{(k_{r,2} - k_{r,1})}{k_{r,2}k_{r,1}} \qquad (31)$$

Equation (30) represents the phase velocity of a frequency. For electromagnetic pulses containing multiple frequencies, a measured velocity is a group velocity of broadband frequency. In general, biologic tissue is dispersive in frequency and the group velocity provides another perspective description for the status of the CSF and brain tissue.

The speed determines the travel time of electromagnetic wave in brain. The speed can be measured using either continuous wave having a single frequency or narrow broadband pulses. Based on the phase velocity, the wave travel time becomes:

$$T = \frac{r}{v} = \frac{rk_r}{\omega} = r\sqrt{\mu\varepsilon} \qquad (32)$$

We define a Travel Time Difference (TTD) based on the propagation velocities:

$$TTD = T_2 - T_1 = \frac{r}{\omega}(k_{r,2} - k_{r,1}) = \frac{1}{\omega}(\phi_2 - \phi_1) \qquad (33)$$

The TTD measures the changes of dielectric constant, which reduces the dependence electrode conductivity and measurement environments.

When the group velocity is used, the estimate of the travel time difference can be benefited by coded signals to increase the sensitivity and minimize the multipath interference. FIG. 6 shows the concept of the time shift between two electrodes due to the wave propagation in the brain tissue.

The complex permittivity $\in = \in' + j\in''$, or dielectric $\in_r$ and conductivity $\sigma$, can be obtained from estimated complex wave number. $k_r$ can be obtained by (25), $k_I$ can be obtained by using transmitted wave amplitude as a reference:

$$k_1 = -\frac{1}{|r|}\log\left(\frac{|2E|}{E_0}\right) \qquad (34)$$

Thus, we can estimate complex wave number $k = k_r + jk_I$. Using the complex wave number, we find complex permittivity using (16) and (7). Thus the dielectric constant $\in_r$ and conductivity can be estimated. Since the magnitude of the field intensity is used in the estimation, the impact of the skin and electrode surface should be noted for the estimation of the conductivity.

FIG. 1 shows the block diagram of the monitoring system for hydrocephalus, cerebral edema, and intracranial bleeding conditions. Prescribed signals 100 are generated and applied to electrodes or coils 101. The signals include continuous signals having a single frequency, broadband pulses having multiple frequencies, and coded signals. The electromagnetic wave transmitted from the transmitting electrodes propagates through brain tissue 102 that includes the brain cavities filled with CSF and brain tissue. Electrodes or coils, or other sensors, 103 on other sides of the brain receive the propagated electromagnetic wave. The received signal is conditioned, amplified, filtered, and converted to digital signal 104. Quadrature detector 105 is applied to obtain in-phase and quadrature signals I and Q, which are used to calculate phase and magnitude by envelope and phase detector 106. Quadrature detector 105 implements the operations of equations (20) and (21). Envelope and phase detector 106 implements the operations of (22) and (23).

With present and early recorded phase and magnitude 106, tissue parameters RAC, RPS, WSC, and TTD 107 are estimated by using equations (24), (26), (31), and (33). The complex wave number and complex permittivity can be also calculated. Estimated RAC, RPS, WSC, TTD, and complex wave number and complex permittivity are used for evaluating conditions of hydrocephalus, cerebral edema, and intracranial bleeding 108. The entire system is controlled by 109.

FIG. 2 illustrates the phase shifts are difference for tissue phantoms having different amounts of blood, measured in a frequency range from 10 kHz to 100 kHz. The measurement frequency range can be lower or higher. The example is only for the illustration purpose.

FIG. 3 illustrates the application of electrodes or coils on a head surface. For example, a transmitting electrode or coils 200 and a receiver electrode or coil 201 are applied in the area that is close to the occipital lobe, another receiving electrode 202 and a reference electrode to ground 203 are applied in temple areas. This configuration is only for illustration purpose. For example, the transmitter and receiver electrodes can be placed anywhere on the head surface. FIG. 3 shows a configuration using four electrodes. Different configurations having different locations of electrodes can be used to measure the parameters of PRS, RAC, MSC, TTD, complex wave number and permittivity, etc. Different configurations use three electrodes or other numbers of electrodes can be used to measure said parameters.

FIG. 4 illustrates the application of receiving electrodes to minimize the impact of the electrodes. The phase shift due to a path length in brain tissue is found by the difference of two quadrature detectors. It is for 4-electrode configuration application. Another electrode is used for transmitting EM wave, and fourth electrode on head surface is also connected to ground for the reference. One of example of these four electrodes are shown in FIG. 3.

FIG. 5 illustrates the 3-electrode configuration where the receiving phase is directly compared with the transmitting phase to obtain the phase shift due to the brain tissue. The third electrode on head surface is also connected to ground for the reference.

FIG. 6 illustrates the time shift between two electrodes when the transmitted electromagnetic wave is coded. Only the envelope of the wave is shown and the carrier frequency does not shown in the figure.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

The invention claimed is:

1. A system for monitoring hydrocephalus, cerebral edema, and intracranial bleeding in noninvasive way, the system comprising:
   at least one signal generator configured to generate an electromagnetic wave;
   at least one source electrode or coil configured to emit the electromagnetic wave to a brain tissue;
   at least one detecting electrode configured to detect said wave that propagates through said brain tissue;
   a digitizer operatively connected to said electrode and configured to digitize a signal detected at said electrode;
   a quadrature detector operatively connected to the digitizer and configured to demodulate the digitized signal and obtain in-phase and quadrature components of the signal;
   an envelope and phase detector operatively connected to the quadrature detector and configured to estimate a magnitude and phase of the signal;
   a special-purpose processor operatively connected to the envelope and phase detector and specially configured to estimate tissue characteristics that are related to status of hydrocephalus, cerebral edema, and intracranial bleeding from the magnitude and phase.

2. The monitoring system as described in claim 1 wherein said source electrode or coil and detecting electrode are configured to be noninvasively applied to skin a surface of head for transmitting and receiving said wave.

3. The monitoring system as described in claim 1 wherein said source electrode or coil comprises an electrode comprising a metal plate, and wherein the detecting electrode comprises a metal plate.

4. The monitoring system as described in claim 1, further comprising an earplug, wherein said source electrode or coil comprises an electrode disposed inside the earplug.

5. The monitoring system as described in claim 1 wherein said source electrode or coil comprises an electrode, and the at least one detecting electrode comprises two electrodes, wherein said envelope and phase detector is configured to obtain a phase difference between signals from said two detecting electrodes, and wherein the processor is specially configured to calculate said tissue characteristics from said phase difference.

6. The monitoring system as described in claim 1 wherein said tissue characteristics related to status of hydrocephalus, cerebral edema, and intracranial bleeding include at least one of: relative attenuation coefficient (RAC), relative phase shift (RPS), Wave Speed Change (WSC), travel time difference (TTD), and complex wave number.

7. The monitoring system as described in claim 6 wherein the special-purpose processor is specially configured to estimate the relative attenuation coefficient (RAC) by comparing the attenuation of said wave propagation through brain tissue to a baseline for assessing status of hydrocephalus, cerebral edema, and intracranial bleeding, wherein the baseline is either an attenuation previously measured or a defined number.

8. The monitoring system as described in claim 6 wherein the special-purpose processor is specially configured to estimate the relative phase shift (RPS) by comparing the phase shift of said wave propagating through said brain tissue to a baseline for assessing status of hydrocephalus, cerebral edema, and intracranial bleeding wherein the baseline is either a phase shift previously measured or a defined number.

9. The monitoring system as described in claim 6 wherein the special-purpose processor is specially configured to estimate the wave speed difference (WSD) by comparing the wave speed difference of said wave propagating through said brain tissue to a baseline for assessing status of hydrocephalus, cerebral edema, and intracranial bleeding, wherein the baseline is either a phase shift previously measured or a defined number.

10. The monitoring system as described in claim 6 wherein the special-purpose processor is specially configured to estimate the travel time difference (TTD) by comparing the travel time of said wave propagation through said brain tissue with a baseline for assessing status of hydrocephalus, cerebral edema, and intracranial bleeding, wherein the baseline is either a travel time previously measured a defined number.

11. The monitoring system as described in claim 1, wherein said signal generator is configured to generate electromagnetic waves from 0 Hz to 100 kHz.

12. The monitoring system as described in claim 6 wherein the processor is specially configured to calculate the complex wave number of brain tissue to assess status of hydrocephalus, cerebral edema, and intracranial bleeding.

13. The monitoring system as described in claim 1 wherein said electromagnetic wave includes continuous wave having a single frequency, broadband pulses having multiple frequencies, and coded wave with prescribed frequencies and wave patterns.

14. The monitoring system of claim 5, the system further comprising a ground reference electrode.

15. The monitoring system of claim 2, where said source electrode or coil comprises an electrode adapted to be in direct contact with the skin surface without insulators between the conductor of the electrodes and tissue surface.

16. The monitoring system of claim 1, further comprising a ground reference electrode, wherein said source electrode or coil comprises an electrode, where said envelope and phase detector is configured to obtain a phase difference between signals at the source (electrode and detecting electrode, and the processor is specially configured to calculate said tissue characteristics from the phase difference.

17. The monitoring system of claim 7, wherein estimating the RAC comprising estimating RAC according to $$RAC = \frac{1}{\omega}(k_{I,2} - k_{I,1})$$

wherein $\omega$ is an angular frequency of the detected electromagnetic wave, $k_{I,1}$ is an imaginary part of a complex wave number $k_1$ from a baseline measurement, and $k_{I,2}$ is an imaginary part of a complex wave number $k_2$ from a measurement of the brain tissue.

18. The monitoring system of claim 8, wherein estimating the RPS comprising estimating RPS according to $$RPS = \frac{1}{\omega}(k_{r,2} - k_{r,1})$$

wherein $\omega$ is an angular frequency of the detected electromagnetic wave, $k_{I,1}$ is an real part of a complex wave number $k_1$ from a baseline measurement, and $k_{I,2}$ is an real part of a complex wave number $k_2$ from a measurement of the brain tissue.

19. The monitoring system of claim 9, wherein estimating the WSD comprising estimating WSD according to $$WSD = \omega \frac{(k_{r,2} - k_{r,1})}{k_{r,2} k_{r,1}}$$

wherein $\omega$ is an angular frequency of the detected electromagnetic wave, $k_{I,1}$ is an real part of a complex wave number $k_1$ from a baseline measurement, and $k_{I,2}$ is an real part of a complex wave number $k_2$ from a measurement of the brain tissue.

20. The monitoring system of claim 10, wherein estimating the TTD comprising estimating TTD according to $$TTD = \frac{r}{\omega}(k_{r,2} - k_{r,1})$$

wherein r is a distance between the source electrode or coil and detecting electrode, $\omega$ is an angular frequency of the detected electromagnetic wave, $k_{I,1}$ is an real part of a complex wave number $k_1$ from a baseline measurement, and $k_{I,2}$ is an real part of a complex wave number $k_2$ from a measurement of the brain tissue.

* * * * *